United States Patent [19]

Chao et al.

[11] Patent Number: 5,085,837

[45] Date of Patent: Feb. 4, 1992

[54] METHOD FOR PURIFYING TIO₂ ORE BY ALTERNATE LEACHING WITH AN AQUEOUS SOLUTION OF AN ALKALI METAL COMPOUND AND AN AQUEOUS SOLUTION OF MINERAL ACID

[75] Inventors: Tze Chao, Newark; George H. Senkler, Jr., Hockessin, both of Del.

[73] Assignee: E. I. Du Pont de Nemours and Company, Wilmington, Del.

[21] Appl. No.: 634,792

[22] Filed: Dec. 27, 1990

Related U.S. Application Data

[62] Division of Ser. No. 225,432, Jul. 28, 1988, Pat. No. 5,011,666.

[51] Int. Cl.⁵ ............................................. C22B 34/10
[52] U.S. Cl. .................................... 423/82; 423/84; 423/85; 423/610; 423/69; 423/86
[58] Field of Search ............. 423/69, 81, 82, 84, 423/112, 139, 50, 85, 54, 64, 49, 2, 131, 610, 86, 21.5, 63

[56] References Cited

U.S. PATENT DOCUMENTS

| | | | |
|---|---|---|---|
| 2,941,863 | 6/1960 | Wainer | 423/71 |
| 3,069,235 | 12/1962 | Schecter et al. | 423/84 |
| 3,816,099 | 6/1974 | Stewart et al. | 75/10.67 |
| 3,856,512 | 12/1974 | Palmer | 423/84 |
| 3,919,388 | 11/1975 | Thompson et al. | 423/76 |
| 4,038,364 | 7/1977 | Lailach | 423/82 |
| 4,176,159 | 11/1979 | Paixao et al. | 423/80 |
| 4,243,179 | 1/1981 | Mangalhaes | 241/24 |
| 4,405,588 | 9/1983 | Caballero et al. | 423/131 |
| 4,759,916 | 6/1988 | Heikel | 423/84 |
| 4,863,711 | 9/1989 | Heikel | 423/82 |
| 5,011,666 | 4/1991 | Chao et al. | 423/86 |

FOREIGN PATENT DOCUMENTS

| | | |
|---|---|---|
| 521914 | 2/1956 | Canada . |
| 1092910 | 4/1955 | France . |
| 1095478 | 6/1955 | France . |
| 48-102712 | 12/1973 | Japan . |
| 49-20688 | 5/1974 | Japan . |
| 54-54914 | 5/1979 | Japan . |
| 725555 | 3/1955 | United Kingdom . |

*Primary Examiner*—Theodore Morris
*Assistant Examiner*—Edward Squillante
*Attorney, Agent, or Firm*—David J. Gould

[57] ABSTRACT

Process for purifying $TiO_2$ ore consisting essentially of subjecting the ore to two or more leaching treatments, said leaching treatments alternating between use of an aqueous solution of a mineral acid and an aqueous solution of an alkali metal compound selected from the group consisting essentially of alkali metal carbonates, hydroxides or mixtures thereof.

26 Claims, No Drawings

METHOD FOR PURIFYING TIO$_2$ ORE BY ALTERNATE LEACHING WITH AN AQUEOUS SOLUTION OF AN ALKALI METAL COMPOUND AND AN AQUEOUS SOLUTION OF MINERAL ACID

This is a division of application Ser. No. 07/225,432, filed July 28, 1988, now U.S. Pat. No. 5,011,666.

BACKGROUND OF THE INVENTION

This invention relates to an improved method for purifying TiO$_2$ ore which contains numerous impurities. The purified ore can be used to make TiO$_2$ pigment or titanium metal or be used in any other process where a purified TiO$_2$ ore is required.

Currently, approximately 75 percent of the titanium minerals produced in the world are utilized by the pigments industry to produce TiO$_2$. In the production of TiO$_2$ by the chloride process, beneficiated ore is used which generally contains about 55–96% TiO$_2$. However, known beneficiation processes do not appear to be capable of satisfactorily purifying TiO$_2$ ore which contains numerous impurities such as alkali metals, alkaline earth metals, rare earth metals, iron, aluminum, phosphorus, thorium, uranium, chromium, manganese, silicon, vanadium, and yttrium. These impurities may be present as oxides, salts, or other complex forms and generally cannot be readily removed by conventional mechanical means or even conventional chemical means. Especially detrimental to the chloride process are such ores which contain in considerable quantity the impurities of iron, calcium, silicon, aluminum, phosphorus, magnesium, barium and strontium, and radionuclides such as thorium and uranium. For example, phosphorus can cause processing problems in the TiO$_2$ process, and thorium and uranium may concentrate in the TiO$_2$ process and present a potential health hazard. Also, the impurities of aluminum, phosphorus, silicon, thorium, and uranium are additionally a problem because they are especially resistant to removal by conventional mechanical or chemical means.

Being able to remove such impurities efficiently would be highly desirable because known sources of TiO$_2$ ore not containing such impurities are becoming increasingly scarce and expensive. Conversely, there exist large bodies of inexpensive carbonatite anatase ores which are rich in TiO$_2$ but also contain significant quantities of such impurities. Moreover, while other processes to purify TiO$_2$ ore are known, it appears that they either require additional, more complex or more expensive processing steps or are deficient in one or more benefits as compared to the process of this invention.

The following information is disclosed which may be of interest to this invention:

U.S. Pat. No. 4,176,159 discloses a process for the removal of impurities from titanium minerals. The process requires high temperature calcining, cooling, reducing, cooling, magnetic separation, mineral acid leaching, neutralizing, and washing.

U.S. Pat. No. 4,038,363 discloses upgrading of titanium values in a slag such as Sorels slag by roasting with an alkali salt, leaching with sulfuric acid in two stages, and calcining.

Japanese patent 48,102,712 discloses dephosphorization of titanium concentrates using caustic alkali after prior removal of iron.

Japanese patent 87-33058/47 discloses production of rutile-type titanium dioxide sol by heat treating hydrated titanium oxide and alkali metal hydroxide and maturing in hydrochloric acid aqueous solution.

SUMMARY OF THE INVENTION

The following summarizes this invention:

Process for purifying TiO$_2$ ore consisting essentially of subjecting the ore to two or more leaching treatments, said leaching treatments:

(a) alternating between use of an aqueous solution of a mineral acid and an aqueous solution of an alkali metal compound selected from the group consisting essentially of alkali metal carbonates, hydroxides or mixtures thereof, (b) being carried out at a temperature, pressure, and time, and with an amount and concentration of an aqueous solution of a mineral acid and an aqueous solution of an alkali metal compound, which are sufficient to solubilize substantially the iron, alkali metal, alkaline earth metal, rare earth metal, aluminum, phosphorous, thorium, uranium, chromium, manganese, silicon, vanadium, and yttrium impurities present to form a leachate, and (c) including a treatment to remove substantially the leachate from the ore prior to the next leaching treatment.

There is also provided by this invention TiO$_2$ which is produced from the purified TiO$_2$ ore of this invention by the chloride process.

In accordance with this invention, it has been found that the aforementioned impurities in TiO$_2$ (and especially iron, calcium, silicon, aluminum, phosphorus, magnesium, barium, strontium and the radionuclides such as thorium and uranium) ore can readily be reduced to acceptable levels. Moreover, the process is especially useful for removing impurities which are resistant to conventional removal means, including aluminum, silicon, phosphorus, thorium, and uranium to acceptable levels. Such purified TiO$_2$ ore is especially suitable for making TiO$_2$ pigment by the chloride process. Finally, the process of this invention is highly useful and desirable because it can make practical the utilization of low grade, inexpensive and more abundant TiO$_2$ ore which contains numerous impurities. The process is also simple and requires few steps. Moreover, the process of this invention can have considerably less energy requirements than many prior art processes because a roasting step prior to leaching generally is not necessary.

DETAILED DESCRIPTION OF THE INVENTION

Ore

It is believed that any TiO$_2$ ore in any form can be used for the process of this invention including anatase, ilmenite and rutile. Preferred is anatase and especially preferred is anatase from a carbonatite source.

The following sets forth the mineral composition of a typical anatase ore which is suitable for being processed in accordance with one process of this invention:

Ti Minerals
 Major: Anatase TiO$_2$
 Minor: Ilmenite FeTiO$_3$ Schorlomite Ca$_3$(Fe, Ti)$_2$(Si, Ti)$_3$O$_{12}$ Ti-pyroxenite (e.g. Ti-Diotite)
Fe Minerals
 Major: Magnetite Fe$_3$O$_4$ Maghemite Y-Fe$_2$O$_3$ Minor: Goethite FeOOH Hematite -$Fe_2O_3$ Ilmenite $FeTiO_3$ Schorlomite $Ca_3(Fe, Ti)_2(Si, Ti)_3O_{12}$ Al Minerals
  Major: Wavellite $Al_6(PO_4)_4(OH)_6.9H_2O$ Crandallite $CaAl_3(PO_4)_2(OH)_5.H_2O$
  Minor: Phlogopite $KMg_3(Si_3AlO_{10})(OH)_2$ Ca Minerals
  Major: Crandallite Hydroxyapatite $Ca_5(PO_4)_3(OH)$ Calcite ($CaCO_3$)
  Minor: Perovskite $CaTiO_3$ Pyroxene (e.g. Diopside)

P and Rare Earth Minerals
  Major: Rhabdophane (La, Nd, Y)($PO_4$).$H_2O$ Crandallite sub-group minerals such as Florencite $CeAl_3(PO_4)_2(OH)_6$
  Minor: Brockite (RE, Th )($PO_4$).$H_2O$ Aeschynite (Ce, Ca, Fe, Th)(Ti, Nb)$_2$(O, OH)$_6$ Other Minerals (gangue)
  Vermiculite $Mg_{11}Al_5FeSi_{11}O_{42}.4OH_2O$
  Quartz $SiO_2$
  Wavellite $Al_6(PO_4)_4(OH)_6.9H_2O$
  Some amorphous phase
  Pyroxenes
  Clay minerals

Impurities

The impurities which can be removed in accordance with the process of this invention include alkali metals, alkaline earth metals, rare earth metals, iron, aluminum, phosphorous, thorium, uranium, chromium, manganese, silicon, vanadium and yttrium. Especially suitable for removal by the process of this invention are the impurities of iron, phosphorus, aluminum, calcium, barium, strontium, chromium, manganese, silicon, vanadium, yttrium, lanthanum, cerium, neodymium, thorium, and uranium. The impurities of phosphorus, silicon, aluminum, iron, calcium, barium, strontium, and radionuclides such as thorium and uranium are especially detrimental to the chloride process for making $TiO_2$ pigment; such impurities can be readily reduced to acceptable levels by the process of this invention. Also, while the impurities of aluminum, phosphorus, silicon, thorium, and uranium are especially resistant to removal by conventional chemical or mechanical means, they can readily be reduced to acceptable levels by the process of this invention. By the term "impurities" is meant the foregoing metals in their elemental state, oxides thereof, salts thereof and other complexes thereof.

Particle Size of Ore

For the process of this invention, preferably, the ore should be in particulate form. The optimum particle size for any $TiO_2$ ore desired to be processed can readily be determined by comminuting (such as by grinding, crushing, milling, etc.) The ore into several different particle sizes and evaluating the amount of impurities removed by the process of this invention.

Generally, it can be desirable to liberate the minerals to be separated from the ore, i.e., to comminute the ore into as fine particles as practical so that the presence of discrete minerals or nearly discrete minerals in the particles is substantially improved, i.e., by at least 10%.

Ordinarily, the ore should have a particle size of less than about one-fourth inch. If ore treated in accordance with this invention is to be used in the chloride process for making $TiO_2$, its particle size can be adjusted so that it is compatible with such process. In such case, the particles preferably will fall within the range of about −20 mesh to +400 mesh. Of course, some ores in their natural state have a particle size within this range. If so, additional comminuting is not necessary.

Mineral Dressing

If desired, the ore can be subjected to mineral dressing prior to the leaching treatments. By mineral dressing is meant mechanical processes which can remove some of the undesired impurities, including desliming (removing fine particles by a cyclone, grating or settling process), crushing, grinding, classification, screening, flotation, electrostatic separation and magnetic separation. Suitable mineral dressing processes are disclosed in U.S. Pat. No. 4,243,179, which is hereby incorporated by reference. If mineral dressing is used, it can be designed to reduce the ore to the desired particle size.

Roasting

Generally, it has been found that for most ores, a roasting prior to the leaching treatments of this invention is not necessary, and if too high a temperature is used, it can be detrimental to the leaching treatments. Consequently, if roasting is used, then preferably a temperature of less than about 700° C., and more preferably less than about 400° C. and most preferably less than 300° C. should be used.

If roasting is used, it can be carried out by any suitable means, process or device. For example, a fixed bed, rotary kiln, fluidized bed, batch or continuous process can be utilized.

Leaching

For the leaching steps, there are utilized two or more leaching treatments, which alternate between use of aqueous solution of a mineral acid and an aqueous solution of an alkali metal compound selected from the group consisting essentially of alkali metal carbonates, hydroxides or mixtures thereof.

Preferred acids are ferric chloride, hydrochloric acid, nitric acid, sulfuric acid, hydrofluoric acid, and mixtures thereof. Especially preferred are hydrochloric acid, nitric acid, hydrofluoric acid, and mixtures thereof. Most especially preferred is hydrochloric acid.

The acid should be utilized in an effective amount, i.e., an amount and concentration sufficient to solublize substantially the impurities. Analysis of the leachate, i.e., the acid solution containing the dissolved impurities, and the leached ore can readily determine whether or not the amount and/or concentration of acid is sufficient. The acid concentration should be at least 1% by weight, based on the total weight of the solution. Ordinarily, the acid will be present in an amount of about 1-40% by weight, based on the total weight of the solution. Preferably, the concentration of the acid will be about 3-35 percent, more preferably about 5-25 percent, and most preferably about 10-20 percent by weight based on the total weight of the solution.

The acid leaching treatment will take place at a temperature and pressure, and for a time which is sufficient to solubilize substantially the mineral impurities present. Ordinarily, the time required will be at least about 10 minutes. Typical ranges of time are about 10 minutes to eight hours, preferably about 15 minutes to four hours and most preferably about 20-40 minutes. The temperature will ordinarily be at least about ambient temperature. Typical temperature ranges are about ambient to 150° C., and most preferably about ambient to 120° C. Ordinarily, the pressure range will be about 1-10 atmospheres absolute, preferably about 1–5 atmospheres absolute, and most preferably about 1–2 atmospheres absolute.

Suitable alkali metal compounds which can be used in the leaching treatment include sodium hydroxide, sodium carbonate, potassium hydroxide, potassium carbonate, lithium hydroxide, and lithium carbonate. Preferred are sodium hydroxide and sodium carbonate. Most preferred is sodium hydroxide.

The alkali metal compound should be used in an effective amount, i.e., an amount and concentration sufficient to solubilize substantially the impurities. Analysis of the leachate, i.e., the solution of the alkali metal compound containing the dissolved impurities, and the leached ore can readily determine whether or not the amount and concentration of alkali metal compound are sufficient. Ordinarily, the concentration of alkali metal compound will be about 2–50 percent, preferably about 10–40 percent, and most preferably about 20 to 30 percent by weight, based on the total weight of the solution.

The leaching treatment with the aqueous solution of an alkali metal compound will take place at a temperature, pressure, and time which is sufficient to solubilize substantially the mineral impurities present. Ordinarily, the time required will be at least about 10 minutes. Typical ranges of time are about 10 minutes to eight hours, preferably about 15 minutes to four hours, and most preferably about 20–40 minutes. The temperature ordinarily will be about 60°–240° C., preferably about 130°–210° C., and most preferably about 180°–210° C. The pressure generally will be about 1–30 atmospheres, preferably about 3–18 atmospheres, and most preferably about 9–18 atmospheres absolute.

In regard to the number of leaching treatments, generally they will not exceed about 10, preferably they will not exceed about 5 and most preferably, they will not exceed about 3. Often, two or three leaching steps will be adequate. Ordinarily, to reduce processing costs, it is desirable to use the fewest steps which will still remove the desired amount of impurities.

By the term "solubilize substantially," as used to describe the leaching treatment, is meant the concentration of acid and alkali metal compound and conditions of temperature, pressure, and time which will solubilize at least about 10% by weight of the total impurities. Preferably, at least 50% of the total impurities will be solubilized. Often, a graph of the concentration of the acid or alkali metal compound and conditions of temperature and time, compared to the amount of impurities removed will help to determine trends and optimizations.

Removing the Leachate

Following each leaching step, the leachate is removed from the treated $TiO_2$ ore. Preferably, this is done by removing the leachate followed by washing with water or by washing with water alone. Preferably, the water will be hot, i.e., up to its boiling point. The amount of washing required can readily be determined by analyzing the wash water for the presence of impurities and acid or alkali metal carbonates of hydroxides.

Use of Treated Ore

After the ore has been treated in accordance with the process of this invention, it can be used to make $TiO_2$ pigment or titanium metal or be used in any process where a purified $TiO_2$ ore is desired. Preferably, the $TiO_2$ ore treated by the process of this invention can be used to make $TiO_2$ pigment, and most preferably, to make $TiO_2$ pigment by the chloride process. Suitable chloride proceses and reactors for using the $TiO_2$ ore treated in accordance with the process of this invention are disclosed in U.S. Pat. Nos. 2,488,439, 2,488,440, 2,559,638, 3,203,763, 2,833,626, 3,284,159, and 2,653,078, which are hereby incorporated by reference.

The following examples illustrate this invention. Unless otherwise indicated, all percentages are percent by weight.

Example I

A flotation concentrate of a titanium ore containing 74.45% $TiO_2$, with the composition shown in Table I, column (a), and with a particle size finer than 200 mesh, was leached with nine times its weight of 20% HCl by stirring for two hours at 90° C. The hot suspension was then filtered and the solids washed with hot water and dried. The dried solid was then leached with 10% NaOH by shaking in a pressure container at about one cycle/two seconds for one hour at 180° C. and 8–10 atmospheres. The pressure container was then vented and opened and the contents filtered hot (ca. 100° C.). The solids were washed with hot $H_2O$ and dried. Analysis of the product is shown in Table I, column (b).

Example II

A flotation concentrate of a titanium ore containing 74.45% $TiO_2$, with the composition shown in Table I, column (a), and with a particle size finer than 200 mesh, was leached with 25% NaOH by shaking in a pressure container at about one cycle/two seconds for one hour at 210° C. and 18 atmospheres. The pressure container was then vented and opened and the contents filtered hot. The solids were washed with hot $H_2O$ and dried. The dried solid was then leached with nine times its weight of 20% HCl by stirring for four hours at 90° C. The hot suspension was then filtered, and the solids washed with hot water and dried. Analysis of th e product is shown in Table I, column (c).

TABLE I

|  | (a) Starting. Material | (b) HCl/ NaOH | (c) NaOH/ HCl |
|---|---|---|---|
| $TiO_2$ (%) | 74.45 | 90.26 | 94.95 |
| $FE_2O_3$ (%) | 4.74 | 4.95 | 1.61 |
| $Al_2O_3$ (%) | 2.97 | 0.10 | 0.00 |
| CaO (%) | 3.60 | 0.42 | 0.20 |
| BaO (%) | 0.28 | 0.17 | 0.05 |
| SrO (%) | 0.21 | 0.10 | 0.00 |
| $Cr_2O_3$ (%) | 0.00 | 0.00 | 0.00 |
| MgO (%) | 0.00 | 0.00 | 0.00 |
| $Nb_2O_5$ (%) | 0.82 | 1.01 | 1.16 |
| $P_2O_5$ (%) | 4.35 | 0.15 | 0.80 |
| $SiO_2$ (%) | 1.03 | 0.83 | 0.49 |
| $V_2O_5$ (%) | 0.13 | 0.10 | 0.06 |
| $ZrO_2$ (%) | 0.37 | 0.41 | 0.37 |
| $Y_2O_3$ (%) | 0.03 | 0.01 | 0.00 |
| $La_2O_3$ (%) | 0.47 | 0.31 | 0.06 |
| $CeO_2$ (%) | 0.94 | 0.64 | 0.08 |
| $Nd_2O_3$ (%) | 0.35 | 0.23 | 0.08 |
| Th (ppm) | 300 | 170 | 35 |
| U (ppm) | 150 | 120 | 20 |

Example III

The starting ore had a typical particle size in minus 10 mesh to plus 170 mesh range, with greater than 70% of the ore particles coarser than 70 mesh. The composition of the starting ore is shown in Table II, column (d).

Forty grams of the starting ore were mixed with 400 milliliters of 20% HCl solution. The slurry was then heated to 90 degrees centigrade under constant agitation of 200 rpm. The leaching was carried out under reflux for 120 minutes. The slurry was then filtered in a Buchner funnel, washed three times with milliliters of hot water, and dried.

Twenty-eight grams of the above HCl-leached ore were then leached again in a caustic solution under the following conditions:
NaOH: 280 milliliters (30%)
Temperature: 210 degrees centigrade
Pressure: approx. 13 atmospheres
Agitation: 200 rpm
Leach Time: 60 minutes After the hydrothermal caustic leaching, the ore was filtered in a Buchner funnel and washed with 200 milliliters hot water at least 3 times, and dried.

Twenty-five grams of the double-leached ore were then finally leached again in HCl under the following conditions:
20% HCl: 250 milliliters
Temperature: 90 degrees centigrade
Agitation: 200 rpm
Leach time: 120 minutes (under reflux)

Chemical analysis of the beneficiated ore samples as well as the starting ore is shown in Table II.

TABLE II

| | Leach | | | (d) |
|---|---|---|---|---|
| | (a) HCl | (b) NaOH | (c) HCl | Starting Material |
| TiO$_2$ | 83.44 | 81.81 | 91.91 | 65.42 |
| Fe$_2$O$_3$ | 4.84 | 4.32 | 3.81 | 13.80 |
| Al$_2$O$_3$ | 2.86 | .31 | .41 | 4.20 |
| CAO | .25 | .23 | .09 | 2.13 |
| BAO | .15 | .14 | .12 | 0.46 |
| SRO | .09 | .08 | .01 | 0.32 |
| CR$_2$O$_3$ | 0 | 0 | 0 | 0 |
| MgO | 0 | 0 | .10 | 0 |
| MnO | .22 | .21 | .18 | 0.61 |
| Nb$_2$O$_5$ | 1.03 | 1.02 | 1.23 | 0.76 |
| P$_2$O$_5$ | 3.28 | .63 | .80 | 5.89 |
| SiO$_2$ | 2.99 | .61 | .67 | 1.69 |
| V$_2$O$_5$ | .12 | .06 | .11 | 0.11 |
| ZRO$_2$ | .47 | .38 | .35 | 0.44 |
| Y$_2$O$_3$ | .02 | .01 | 0 | 0.05 |
| La$_2$O$_3$ | .21 | .20 | .09 | 0.61 |
| CeO$_2$ | .50 | .48 | .21 | 1.18 |
| NdO$_3$ | .12 | .11 | .01 | 0.47 |
| TH (ppm) | 168 | 168 | 92 | 325 |
| U (ppm) | 96 | 91 | 55 | 120 |

What is claimed is:

1. Process for purifying TiO$_2$ ore containing impurities of iron, alkali metal, alkaline earth metal, rare earth metal, aluminum, phosphorus, thorium, uranium, chromium, manganese, silicon, vanadium, and yttrium, said process consisting essentially of subjecting the ore to two or more leaching treatments, said leaching treatments:

(a) alternating between use of an aqueous solution of a mineral acid and an aqueous solution of an alkali metal compound selected from the group consisting essentially of alkali metal carbonates, hydroxides or mixtures thereof, and wherein the treatment with an aqueous solution of an alkali metal carbonate occurs first, and (b) being conducted at a temperature, pressure, and time, and with an amount and concentration of an aqueous solution of a mineral acid and an aqueous solution of an alkali metal compound, which are sufficient to solubilize substantially the iron, alkali metal, alkaline earth metal, rare earth metal, aluminum, phosphorus, thorium, uranium, chromium, manganese, silicon, vanadium, and yttrium impurities present to form a leachate, and wherein the leachate formed is removed prior to the next leaching treatment.

2. The process of claim 1 wherein the alkali metal compound used for the leaching treatment consists essentially of sodium hydroxide, sodium carbonate or mixtures thereof, and the mineral acid used for the leaching treatment consists essentially of hydrochloric acid, sulfuric acid, nitric acid, hydrofluoric acid or mixtures thereof.

3. The process of claim 2 wherein the alkali metal compound used for the leaching treatment is present in an amount of about 2-50% by weight, based on the total weight of the solution; the mineral acid used for the leaching treatment is present in an amount of about 1-40% by weight, based on the total weight of the solution; and the TiO$_2$ ore has a particle size of about −20 mesh to +400 mesh.

4. The process of claim 3 wherein the alkali metal compound used for the leaching treatment is present in an amount of about 10-40% by weight, based on the total weight of the solution, and the mineral acid used for the leaching treatment is present is an amount of about 3-35% by weight, based on the total weight of the solution.

5. The process of claim 3 wherein the alkali metal compound used for the leaching treatment is present in an amount of about 20-30% by weight, based on the total weight of the solution, and the mineral acid used for the leaching treatment is present in an amount of about 5-25% by weight, based on the total weight of the solution.

6. The process of claim 3 wherein the alkali metal compound is sodium hydroxide which is present in an amount of about 10-40% by weight, and the acid is hydrochloric acid which is present in an amount of about 3-35% by weight.

7. The process of claim 1 wherein prior to the leaching treatments the ore is subjected to mineral dressing; the leaching treatment with an aqueous solution of a mineral acid takes place at a temperature of about ambient to about 150° C., a pressure of about 1-10 atmospheres, and for a time of about 10 minutes to about 8 hours; the leaching treatment with a solution of an alkali metal compound takes place at a temperature of about 60°-240° C., a pressure of about 1-30 atmospheres, and a time of about 10 minutes to about 8 hours; and the removal of the leachate includes washing with water.

8. The process of claim 2 wherein prior to the leaching treatments the ore is subjected to mineral dressing; the leaching treatment with an aqueous solution of a mineral acid takes place at a temperature of about ambient to about 150° C., a pressure of about 1-10 atmospheres, and for a time of about 10 minutes to about 8 hours; the leaching treatment with an aqueous solution of an alkali metal compound takes place at a temperature of about 60°-240° C., a pressure of about 1-30 atmospheres, and a time of about 10 minutes to about 8 hours; and the removal of the leachate includes washing with water.

9. The process of claim 3 wherein prior to the leaching treatments the ore is subjected to mineral dressing; the leaching treatment with an aqueous solution of a mineral acid takes place at a temperature of about ambient to about 150° C., a pressure of about 1-10 atmospheres, and for a time of about 10 minutes to about 8 hours; the leaching treatment with an aqueous solution of an alkali metal compound takes place at a temperature of about 60°-240° C., a pressure of about 1-30 atmospheres, and a time of about 10 minutes to about 8 hours; and the removal of the leachate includes washing with water.

10. The process of claim 4 wherein prior to the leaching treatments the ore is subjected to mineral dressing; the leaching treatment with an aqueous solution of a mineral acid takes place at a temperature of about ambient to about 150° C., a pressure of about 1-10 atmospheres, and for a time of about 10 minutes to about 8 hours; the leaching treatment with an aqueous solution of an alkali metal compound takes place at a temperature of about 60°-240° C., a pressure of about 1-30 atmospheres, and a time of about 10 minutes to about 8 hours; and the removal of the leachate includes washing with water.

11. The process of claim 5 wherein prior to the leaching treatments the ore is subjected to mineral dressing; the leaching treatment with an aqueous solution of a mineral acid takes place at a temperature of about ambient to about 150° C., a pressure of about 1-10 atmospheres, and for a time of about 10 minutes to about 8 hours; the leaching treatment with an aqueous solution of an alkali metal compound takes place at a temperature of about 60°-240° C., a pressure of about 1-30 atmospheres, and a time of about 10 minutes to about 8 hours; and the removal of the leachate includes washing with water.

12. The process of claim 7 wherein the ore is anatase; prior to the leaching treatments the ore is subjected to mineral dressing; the leaching treatment with an aqueous solution of a mineral acid takes place at a temperature of about ambient to about 150° C., a pressure of about 1-10 atmospheres, and for a time of about 10 minutes to about 8 hours; the leaching treatment with an aqueous solution of an alkali metal compound takes place at a temperature of about 60°-240° C., a pressure of about 1-30 atmospheres, and a time of about 10 minutes to about 8 hours; and the removal of the leachate includes washing with water.

13. The process of claim 7 wherein the leaching treatment with an aqueous solution of an alkali metal compound takes place at a temperature of about 130°-210° C. and a pressure of about 3-18 atmospheres.

14. The process of claim 8 wherein the leaching treatment with an aqueous solution of an alkali metal compound takes place at a temperature of about 130°-210° C. and a pressure of about 3-18 atmospheres.

15. The process of claim 9 wherein the leaching treatment with an aqueous solution of an alkali metal compound takes place at a temperature of about 130°-210° C. and a pressure of about 3-18 atmospheres.

16. The process of claim 12 wherein the leaching treatment with an aqueous solution of an alkali metal compound takes place at a temperature of about 130°-210° C. and a pressure of about 3-18 atmospheres.

17. The process of claim 11 wherein the leaching treatment with an aqueous solution of an alkali metal compound takes place at a temperature of about 130°-210° C. and a pressure of about 3-18 atmospheres.

18. The process of claim 12 wherein the leaching treatment with an aqueous solution of an alkali metal compound takes place at a temperature of about 130°-210° C. and a pressure of about 3-18 atmospheres.

19. The process of any one of claims 1-18 wherein the total number of leaching treatments does not exceed about 10.

20. The process of any one of claims 1-18 wherein the total number of leaching treatments does not exceed about 5.

21. The process of any of claims 1-18 wherein the total number of leaching treatments does not exceed about 3.

22. The process of any of claims 1-18 wherein the total number of leaching treatments does not exceed about 2.

23. The process of any of claims 1-18 wherein the first leaching treatment uses an aqueous solution of an alkali metal compound, and the total number of leaching treatments does not exceed about 10.

24. The process of any of claims 1-18 wherein the first leaching treatment uses an aqueous solution of an alkali metal compound, and the total number of leaching treatments does not exceed about 5.

25. The process of any of claims 1-18 wherein the first leaching treatment uses an aqueous solution of an alkali metal compound, and the total number of leaching treatments does not exceed about 3.

26. The process of any of claims 1-18 wherein the first leaching treatment uses an aqueous solution of an alkali metal compound, and the total number of leaching treatments does not exceed 2.

* * * * *